United States Patent
Tominaga et al.

(10) Patent No.: US 6,423,049 B1
(45) Date of Patent: Jul. 23, 2002

(54) DISPOSABLE DIAPER WITH MECHANICAL FASTENING MEMBERS

(75) Inventors: Yutaka Tominaga; Toshiaki Takizawa; Mitsuru Akeno; Ryoichiro Uehara, all of Toyama-ken (JP)

(73) Assignee: YKK Corporation, Tokyo (JP)

( * ) Notice: Subject to any disclaimer, the term of this patent is extended or adjusted under 35 U.S.C. 154(b) by 0 days.

(21) Appl. No.: 09/628,898

(22) Filed: Jul. 31, 2000

(30) Foreign Application Priority Data

Aug. 12, 1999 (JP) .......................................... 11-228413

(51) Int. Cl.[7] .................................................. A61F 13/15
(52) U.S. Cl. ........................ 604/392; 604/386; 604/387; 604/394; 604/396
(58) Field of Search .................................. 604/358, 367, 604/385.01, 385.03, 385.13, 385.21, 385.23, 385.24, 385.29, 385.3, 399, 396, 394, 386, 385.28; 24/437, 320, 374, 542, 575, 578, 580, 598.1, 610, 615, 629

(56) References Cited

U.S. PATENT DOCUMENTS

| | | | | |
|---|---|---|---|---|
| 1,607,085 A | * | 11/1926 | Kilstrom | 24/615 |
| 2,294,617 A | * | 9/1942 | Horowitz | 24/201 |
| 2,548,162 A | * | 4/1951 | Karels | 128/284 |
| 2,837,096 A | * | 6/1958 | Leveillee | 128/284 |
| 3,430,306 A | * | 3/1969 | Tareau | 24/230 |
| 3,882,871 A | | 5/1975 | Taniguchi | 128/287 |
| 4,701,179 A | * | 10/1987 | Kellenberger et al. | 604/394 |
| 6,123,695 A | * | 9/2000 | Skog et al. | 604/368 |

* cited by examiner

Primary Examiner—John G. Weiss
Assistant Examiner—Jacqueline F Stephens
(74) Attorney, Agent, or Firm—Finnegan, Henderson, Farabow, Garrett & Dunner, LLP

(57) ABSTRACT

The present invention provides a disposable diaper, which is easy to put on the wearer, and which is possible to be put on easily while the wearer is standing on both legs. The disposable diaper according to the present invention includes a diaper body having a hip portion and a belly portion, which are spread out with a crotch portion between them. The diaper further includes male members which are protrusively arranged from side portions of one of the hip portion and said belly portion in a face direction and female members, which are arranged on side portions of the other and in which the male members engage in a face direction of the side portions. The female members are provided with receiving portions in which the male members are inserted in a face direction of the side portions. Engaged surfaces perpendicular to the inserting direction of the male member are formed on the inner walls of the receiving portions and the male members are provided with engaging surfaces opposing to the engaged surfaces.

4 Claims, 4 Drawing Sheets

DISPOSABLE DIAPER WITH MECHANICAL FASTENING MEMBERS

BACKGROUND OF THE INVENTION

1. Field of the Invention

The present invention relates to a disposable diaper, which is disposed after use.

2. Description of the Related Art

As a conventional disposable diaper, a spread out type disposable diaper is designed with a hip portion to cover a wearer's hip and a belly portion to cover the wearer's belly. In this spread out type disposable diaper, the hip portion and the belly portion are spread apart and they are composed attachably/detachably. The spread out type disposable diaper comprises a sheet-shaped diaper body, which encloses an absorbent polymer or the like therein. When the wearer uses this diaper, the sheet-shaped diaper body is formed as a stereoscopic shape so that the diaper obtains a pants-like shape. In the spread out type disposable diaper, the diaper body is composed of the hip portion, a crotch portion and the belly portion provided integrally and continuously. At the both sides of the hip portion, adhesive tapes are disposed to extend to the outside. The adhesive tapes are held in tentative attaching portions made of a film or the like, which are provided on the hip portion before assembling the diaper. When the diaper is put on, the adhesive tapes are secured to the belly portion.

As for conventional disposable diapers, a pants-shaped diaper has been used. This pants-shaped disposable diaper is designed such that the wearer can put it on, as the wearer is standing. The wearer inserts his legs into leg-through holes from the inside to the outside of the diaper for each leg and the diaper can be pulled up to the wearer's waist, as if the wearer puts a pants on.

The conventional spread out type disposable diaper, which is provided with a hook shaped connecting member, is disclosed in Japanese Patent No. 2525779. This disposable diaper is provided with a first fastener member with a plate shape inside of both sides of a hip portion. This first fastener member is folded back toward the inside of the hip portion. Further, being opposed to the first fastener member at the sides of an outside of a belly portion, a second fastener member of a plate shape is provided. This second fastener member is folded back toward the front side of the belly portion. In the first fastener member and the second fastener member, the respective folded portions extend away from a disposable diaper body, the respective medium portions curve toward the surface of the disposable diaper body and the respective front portions are folded away from the disposable diaper body. As a result, the first fastener member and the second fastener member become substantially in the shape of the letter S. In this conventional disposable diaper, the sides of the hip portion and the belly portion are sufficiently overlapped to engage the first fastener member and the second fastener member, so that the disposable diaper body is formed in a stereoscopic shape.

In the foregoing conventional arts, the spread-out type disposable diaper cannot be worn while the wearer is standing. The wearer has to be laid to put the diaper on, which is laborious and also requires a space enough to lay the wearer down. Therefore, it is quite inconvenient at the time of going outside. The pants-shaped disposable diaper is designed such that the wearer can put it on, as the wearer is standing. However, the wearer inserts his legs into leg-through holes from the inside to the outside of the diaper, so it is difficult to put it on with shoes on.

On the other hand, according to the disposable diaper disclosed in Japanese Patent No. 2525779, when the first fastener member and the second fastener member are engaged, it is necessary to engage the sides of the hip portion and the belly portion after pulling them up sufficiently till the first fastener member pass over the second fastener member. Therefore, force is needed and it gives a feeling of pressing to the wearer. Further, it is hard to attach the fastener members and to put on.

SUMMARY OF THE INVENTION

The present invention provides a disposable diaper including a diaper body having a hip portion and a belly portion, which are spread out with a crotch portion between them, a male member which is in the shape of thin plate and which are protrusively arranged on side portions of one of the hip portion and the belly portion, and a female member which is relatively thin and arranged on side portions of the other. And the female members are engaged with the male members in the direction of the surfaces of the side portions. Preferably, the female members are provided with receiving portions, in which the male members are inserted in parallel to a face of the side portions. Engaged surfaces engaging with engaging surfaces of the male member are formed in inner walls of the receiving portion.

Preferably, the engaging surfaces are inner end faces of projecting portions projecting from upper and lower inner surfaces of the receiving portion.

Also preferably, the female members are provided with the receiving portions in which the male members are inserted. The engaged surfaces are formed on the inner walls of the receiving portions, being opposed with respect to the direction that the male members are inserted and being alternately arranged along the direction that the male members are inserted. The male members are provided with the engaging surfaces, which are opposed to the engaged surfaces.

With the disposable diaper of the present invention, the both side portions of the hip portion and the side portions of the belly portion are positioned at the outside of the wearer's legs so that the male members are inserted into the female members to be engaged each other. Accordingly, the engaging surfaces of the male members come in contact with the engaged surfaces of the female members to be engaged each other, so that the male members and the female members are connected. Therefore, the disposable diaper of the present invention can be formed in a stereoscopic shape for use. In this state, it is possible to pull up the disposable diaper to the wearer's waist.

DESCRIPTION OF THE PREFERRED EMBODIMENTS

Figure 1:
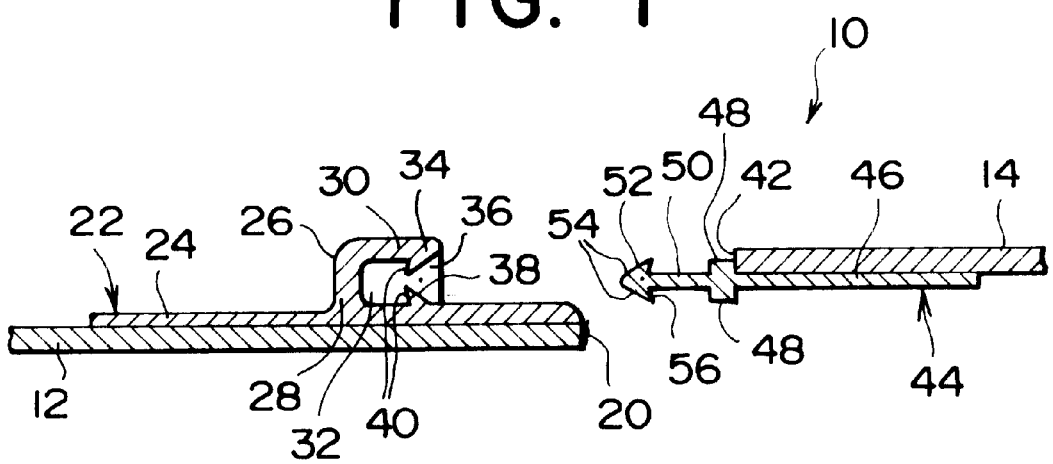
FIG. 1 is a cross sectional view of both side portions of a disposable diaper according to a first embodiment of the present invention.
Figure 2:
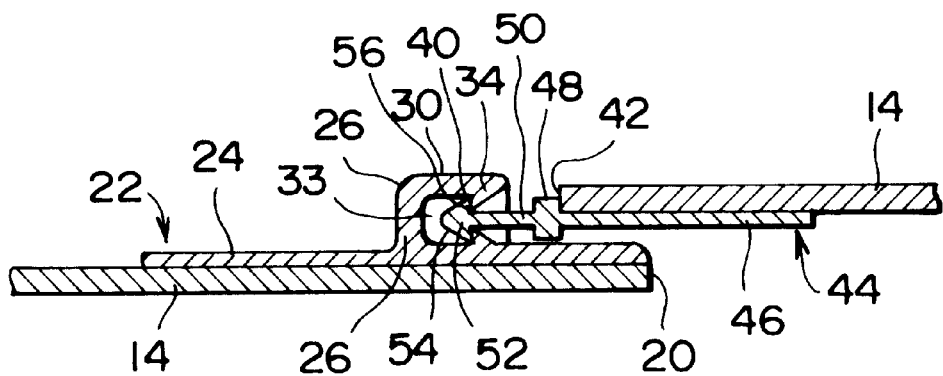
FIG. 2 is a cross sectional view for illustrating the side portions of the disposable diaper according to the first embodiment, which are connected each other.
Figure 3:
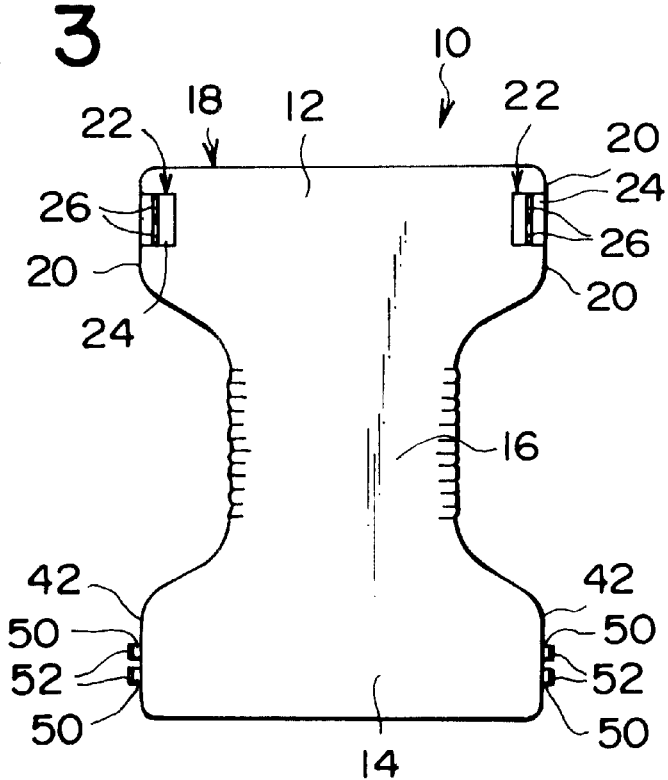
FIG. 3 is a plan view of the disposable diaper according to the first embodiment.
Figure 4:
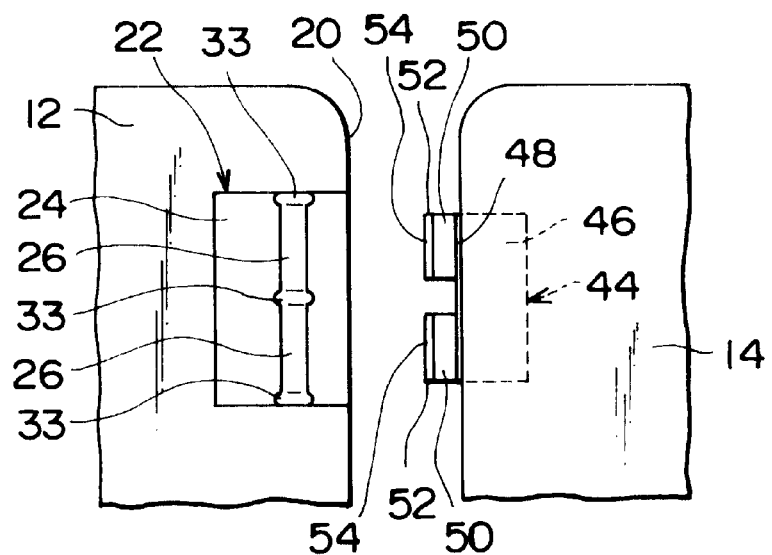
FIG. 4 is a plan view of the side portions at the right side of the wearer, of the disposable diaper according to the first embodiment.

Embodiments of the present invention will be explained below with reference to the drawings. FIGS. 1 to 4 illustrate a first embodiment of the present invention. A disposable diaper 10 according to this embodiment of the present invention comprises a diaper body 18, which is composed integrally with a hip portion 12 to cover the wearer's hip, a belly portion 14 to cover the wearer's belly and a narrow crotch portion 16 positioned between the hip portion 12 and the belly portion 14. The diaper body 18 is configured such that a waterproof cover sheet is provided on the outside thereof and an absorbent body made of an absorbent polymer is disposed on the inside, namely, the side which the body touches. Further, a liquid-permeable sheet is disposed on the surface of the absorbent body. FIG. 3 shows the diaper body 10 with a view of the outside of the diaper body 18, namely, showing the cover sheet.

The disposal diaper according to the present embodiment is provided with female members 22, which are made of synthetic resin with appropriate elastic force, at the outside of the hip portion 12 in both side portions 20. The female members 22 are provided with a pair of engaged portions 26, which are arranged in parallel with the side portions 20, are formed integrally on a base plate 24 mounted on the hip portion 12. Further, the engaged portions 26 are in the shape of a narrow strip elongated in a direction parallel to the side portions 20. A sectional shape in a longitudinal direction of the engaged portions 26 i.e. perpendicular to an edge of the side portion show a rising portion 28, which is rising substantially perpendicular to the base plate 24 as shown in FIG. 1. An end portion of the rising portion 28 is provided with an upper surface portion 30 in integrate with the rising portion 28. The upper surface portion 30 extends to the edge of the side portion 20 to be in parallel with the base plate 24. Between the upper surface portion 30 and the base plate 24, an opening 36, in which an engaging projection 50 can be inserted, and a receiving portion 32, which communicates with the opening 36, are formed, respectively. With respect to the engaging projection 50, the explanation thereof will be given later. Near an end portion of the receiving portion 32 at the side of the edge of the both side portion 20, projecting portions 34 are disposed on the upper surface portion 30 and the plate 24, respectively. The projecting portions 34 are projecting to the center of the receiving portion 32. The cross section of the projecting portion 34 is in a triangular shape, which projects to the inside of the receiving portion 32. A surface of the projecting portion 34 on the side of the opening 36 is defined to be a contact surface 38, which is an inclined plane, approaching toward inner side of the receiving portion 32 as it goes away from the opening 36. A surface of the projecting portion 34 away from the opening 36 is defined to be an engaged surface 40, which is substantially perpendicular to the base plate 24. Further, the engaged portions 26 are deformed toward the side of the base plate 24 by melting to form welded portions 33 at opposite longitudinal end portions and the central portion of the receiving portion 32, in parallel with the side portions 20.

At both side portions 42 of the belly portion 14, male members 44 are disposed, which are made of synthetic resin and which have appropriate elastic force. The male member 44 includes a base plate 46 on the inside of the belly portion 14. A front side and a rear side of the base plate 46 are provided with a positioning projection 48 to abut to the side portion 42. Further, from the positioning projection 48 to the outside thereof, a pair of engaging projections 50 are formed on the elongation of the base plate 46 in parallel, which protrude sideways from the side portion 42. At a front end of the engaging projection 50, an engaging portion 52 of an arrow shape is formed. The engaging portion 52 is thick in the direction perpendicular to the protruding direction of the engaging projection 50. Surfaces at the end side of the engaging portion 52 serve as contact surfaces 54 which are inclined surfaces formed of the surfaces of the engaging projection 50 are approaching each other toward the front end. The side face of the engaging portion 52 away from the front end of the engaging projection 50 is defined to be engaging surfaces 56, which are substantially perpendicular to the engaging projection 50.

The female member 22 and the male member 44 can be obtained by cutting a molded member, which is continuously and integrally molded by extrusion on molding of synthetic resin material in a sheet shape, with a desired length in a longitudinal direction. Further, the female member 22 is formed by cutting the shaping member in a predetermined size and then, the welded portions 33 are formed by heat-melting means. The male member 44 can be easily formed by hollowing out the center of a portion for forming the pair of engaging projections 50 at the same time of cutting the molded member in a predetermined size.

A method for using the disposable diaper 10 according to the present embodiment will be explained below. At first, as an infant is standing who is the wearer, the crotch portion 16 of the diaper body 18 is positioned between both legs near the bottom of the legs of the wearer. The side portions 20 of the hip portion 12 and the side portions 42 of the belly portion 14 are closed each other at the outside of wearer's legs. Then, the engaging projection 50 of the male member 44 on the belly portion 14 is inserted into the opening 36 of the female member 22 on the hip portion 12. At that time, the contact surfaces 54 of the engaging projections 50 make the contact surfaces 38 of the opening 36 open, so that the engaged portion 26 of the female member 22 is elastically deformed. Therefore, the engaging portion 52 of the male member 44 climbs over the projecting portion 34 of the female member 22 so that the engaging projection 50 of the male member 44 can be accommodated in the receiving portion 32 of the female member 22. Accordingly, the engaging surfaces 56 and the engaged surfaces 40 come in contact with each other to be engaged as shown in FIG. 2. As a result, in the diaper body 18, the side portions 20 of the hip portion 12 and the side portions 42 of the belly portion 14 are engaged each other at the outside of the wearer's legs. Accordingly, the diaper body 18 obtains a stereoscopic shape for the use. At this time, the wearer's legs are inserted into leg-through holes, which are formed by bending the diaper body 18. In this state, the diaper 10 can be pulled up to the waist of the wearer.

According to the disposable diaper 10 of the present embodiment, it is possible to easily form the spread out type diaper into a stereoscopic shape while the wearer is standing. Since the female members 22 and the male members 44 can be engaged reliably and can be connected firmly, due to the elastic force of the synthetic resin, the spread out type diaper of the present embodiment can be pulled up to the waist of the wearer like a pant type diaper. Further, when assembling the disposable diaper 10, the leg-through holes can be formed as the wearer is standing with his legs being inserted into the leg-through holes. Therefore, with the wearer's shoes on, it is possible to put on the disposable diaper 10 easily. When the wearer puts on the disposable diaper 10 outdoors, sand or the like does not enter the diaper. The pair of the engaged portions 26 of the female member 22 and the pair of the engaging projection 50 of the male member 44 are provided, respectively and the opposite ends of the receiving portions 32 of the engaged portions 26 are provided with the welded portions 33, so that the engaging projections 50 of the male members 44 are not disengaged from the female member 22 during the use of the disposable diaper 10. Further when putting on the disposable diaper 10, the positioning of the height of the hip portion 12 and the belly portion 14 can be reliably performed each other. Therefore, it is easy to form the disposable diaper 10 into the appropriate shape. Since the direction for inserting the engaging portion 52 is identical with the face direction of the side portion 20, it is possible to make the configuration of the disposable diaper 10 thinner and the wearer can put it on easily.

Figure 5:
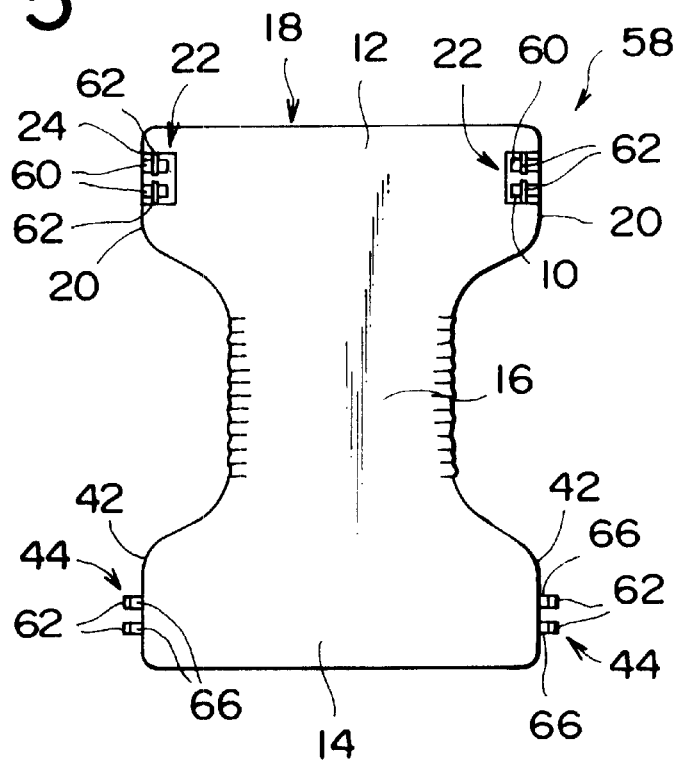
FIG. 5 is a plan view of the disposable diaper according to a second embodiment of the present invention.
Figure 6:
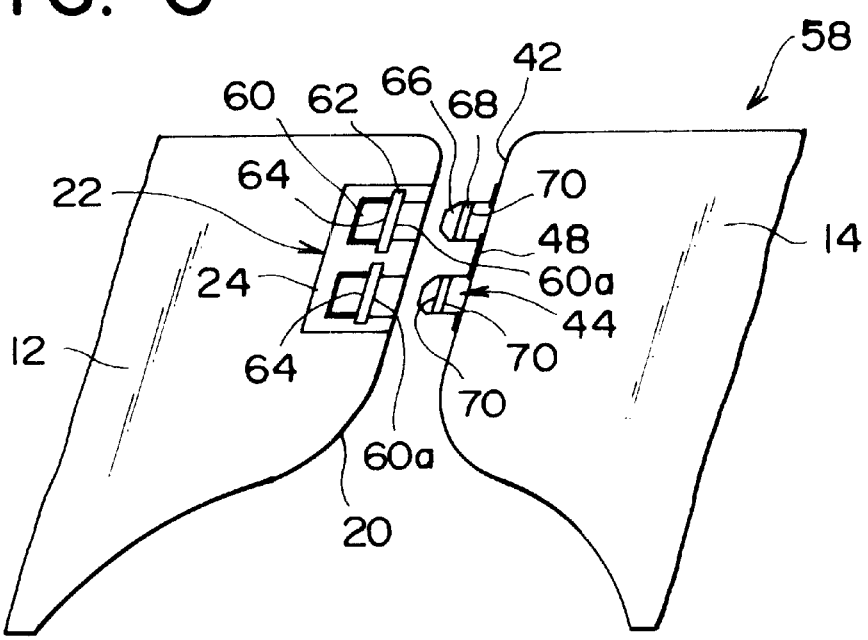
FIG. 6 is a partial perspective view of the side portions of the disposable diaper according to the second embodiment.
Figure 7:
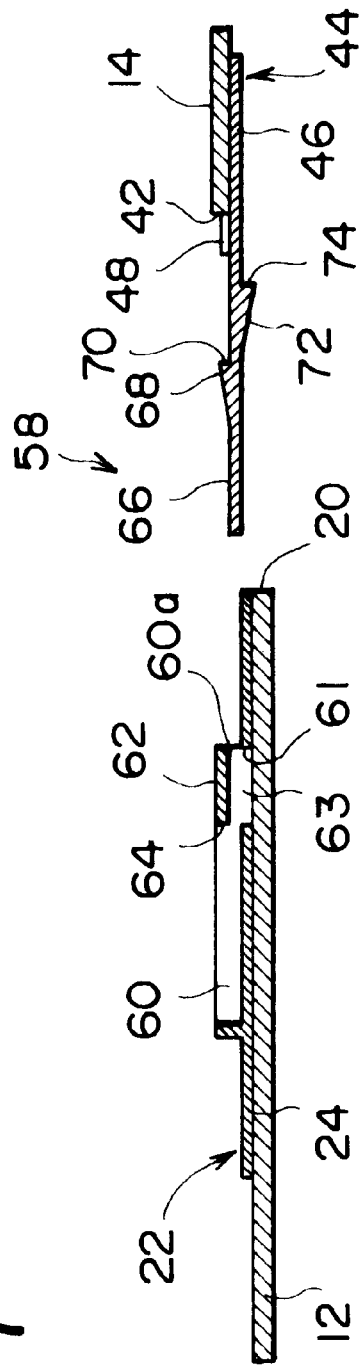
FIG. 7 is a cross sectional view of the side portions of the disposable diaper according to the second embodiment.
Figure 8:
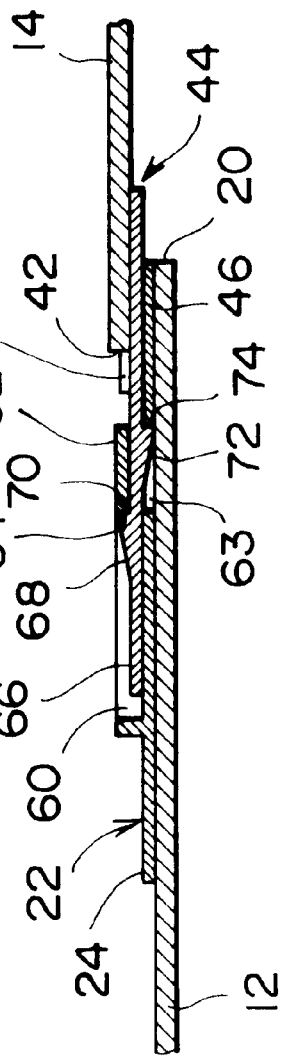
FIG. 8 is a cross sectional view for illustrating the side portions of the disposable diaper according to the second embodiment, which are connected each other.

A second embodiment of the present invention will be explained below with reference to FIGS. 5 to 8. In the disposable diaper 58 of the present embodiment, with respect to the identical members as those of the first embodiment, the identical reference numbers are applied and the explanation thereof is herein omitted. As shown in FIG. 5, the female member 22 which is made of synthetic resin and which owns appropriate elastic force is disposed near the side portion 20 at the outside of the hip portion 12. As shown in FIG. 6, the female member 22 is provided with a pair of guide grooves 60 on the base plate 24, which is disposed on the hip portion 12. The pair of guide grooves 60 is in parallel with the side portion 20 and has openings 60a, which communicate with the side portion 20. The longitudinal direction of the guide grooves 60 is perpendicular to the side portion 20. Further, near the center of the guide grooves 60, engaged portions 62 in a bar shape are disposed perpendicular to the longitudinal direction of the guide grooves 60. The engaged portions 62 are disposed on the surface of the base plate 24 following the guide grooves 60. The edges of the engaged portions 62 at the side of the guide grooves 60 are defined with engaged surfaces 64, to which engaging projections 66, which will be described later, are engaged. The openings 60a of the engaged portions 62 communicate with the guide grooves 60 via the inside of the engaged portions 62. As shown in FIG. 7, in the inside of the opening 60a, an engaged surface 61 is defined by a step portion formed by a through hole 63 in the base plate 24. The guide groove 60 and the through hole 63 serve as the receiving portion 32 of the invention. The engaged surface 61 is engaged with the engaging projection 66.

On the other hand, both side portion 42 of the belly portion 14 is provided with the male member 44, which is made of synthetic resin and which has appropriate elastic force. The male member 44 includes a base plate 46, which is disposed on the inside of the belly portion 14. A pair of the engaging projections 66 which extend from the base plate 46 and projects out from both side portion 42 sideways are formed in parallel. Near the center of the engaging projection 66, a projecting portion 68 in the arrow shape in section is formed with a difference in level in parallel with respect to both side portion 42. The side portion of the projecting portion 68 is formed in a slope, which approaches the surface of the base plate 46 along the direction of projection. A step portion facing the side portion 42 forms an engaging surface 70. Further, also on an surface of the engaging projections 66 opposite to the projecting portion 68, a projecting portion 72 is formed at a position not corresponding to the projecting portion 68, which is defined with an engaged surface 74 and has the same shape as that of the projecting portion 68. The projecting portion 72 is positioned nearer to the side portion 42 than the projecting portion 68.

A method for using the disposable diaper 58 according to the present embodiment will be explained below. At first, the side portion 20 of the hip portion 12 and the side portion 42 of the belly portion 14 are closed each other at the outside of wearer's legs. Then, the engaging projection 66 of the male member 44 on the belly portion 14 is inserted into the opening 60a of the female member 22 on the hip portion 12. With respect to the engaging projection 66 of the male member 44, the projecting portion 68 thereof passes under the engaged portion 62 of the female member 22 through the opening 60a, so that the engaging projection 66 is accommodated in the guide groove 60. Then, the engaging surface 70 comes in contact with the engaged surface 64. The engaging surface 74 comes in contact with the engaged surface 61 to be engaged each other. As a result, in the diaper body 18, the side portions 20 of the hip portion 12 and the side portions 42 of the belly portion 14 are connected each other at the outside of the wearer's legs. Accordingly, the diaper body 18 obtains a stereoscopic shape for the use.

According to the disposable diaper 58 of the present embodiment, the same effect as that of the above embodiment can be realized. Further, with respect of the present embodiment, the projecting portions 68 and 72 of the engaging projection 66 are positioned alternately and the engaging projection 66 and the engaged portion 62 are engaged more reliably and strongly than that of the first embodiment. The projecting portion 72 is positioned within the through hole 63 of the base plate 24 and allows the thickness of the wall of the female member 22 to be thinner.

The disposable diaper according to the present invention may not be limited to respective embodiments as set forth above. For example, the male member and the female member may be disposed on any one of the hip portion or the belly portion. The male member and the female member also may be disposed on the hip portion and the belly portion, respectively. Further, the number or the shape of the engaging projections or the like can be modified freely. Appropriate pick-up pieces may be provided near the openings of the female member. Accordingly, picking up the pick-up pieces allows the openings to be elastically deformed, so that it can be easier to disengage the male members from the female members. Further, the wearer of the disposable diaper according to the present invention may be a baby or an adult in addition to an infant. The disposable diaper according to the present invention may be put on when the wearer is standing, or the wearer lies down.

According to the disposable diaper of the present invention, it is convenient for the wearer to be capable of putting on the disposable diaper while the wearer is standing on both legs. Further, according to the disposable diaper of the present invention, when making the diaper body into a stereoscopic shape, it is possible to connect the hip portion and the belly portion reliably at the appropriate portion each other. It is also possible to make the configuration of the disposable diaper thinner so that the wearer can put it on comfortably.

What is claimed is:
1. A disposable diaper comprising:
   a diaper body having a hip portion and a belly portion, which are spread out with a crotch portion between them a male member which protrudes outwardly from side portions of one of said hip portion and said belly portion in the same plane as that of said side portions; and a female member which is arranged on side portions of the other of said hip portion and said belly portion and in which said male member is substantially enclosed in a face direction of said side portions.

2. A disposable diaper according to claim 1, wherein said female member is provided with a receiving portion, in which said male member is inserted in parallel to a face direction of said side portions, engaged surfaces engaging with engaging surfaces of the male member are formed on an inner wall of said receiving portion.

3. A disposable diaper according to claim 2, wherein said engaged surfaces are inner end faces of projecting portions projecting from upper and lower inner surfaces of said receiving portion.

4. A disposable diaper according to claim 2, wherein said female member is provided with said receiving portion, in which said male member is inserted, said engaged surfaces opposing with respect to the inserting direction of said male member are formed on the inner wall of said receiving portion alternately in the insertion direction and said male member is provided with said engaging surfaces opposing to said engaged surfaces.

* * * * *